(12) United States Patent
Spreizer

(10) Patent No.: US 9,145,217 B2
(45) Date of Patent: Sep. 29, 2015

(54) DEVICE AND METHOD FOR THE MULTIPLE FILLING OF HIGH-VISCOSITY MATERIALS

(75) Inventor: Heinrich Spreizer, Ermatingen (CH)

(73) Assignee: Dentsply International Inc., York, PA (US)

( * ) Notice: Subject to any disclaimer, the term of this patent is extended or adjusted under 35 U.S.C. 154(b) by 19 days.

(21) Appl. No.: 13/883,227

(22) PCT Filed: Nov. 2, 2011
(Under 37 CFR 1.47)

(86) PCT No.: PCT/EP2011/069216
§ 371 (c)(1),
(2), (4) Date: Oct. 23, 2013

(87) PCT Pub. No.: WO2012/059504
PCT Pub. Date: May 10, 2012

(65) Prior Publication Data
US 2014/0238528 A1    Aug. 28, 2014

(30) Foreign Application Priority Data
Nov. 2, 2010 (DE) .................. 10 2010 060 308

(51) Int. Cl.
| B65B 3/14 | (2006.01) |
| B65B 3/00 | (2006.01) |
| B65B 3/12 | (2006.01) |
| B65B 3/32 | (2006.01) |
| B65B 43/59 | (2006.01) |

(52) U.S. Cl.
CPC . B65B 3/14 (2013.01); B65B 3/003 (2013.01); B65B 3/12 (2013.01); B65B 3/32 (2013.01); B65B 43/59 (2013.01)

(58) Field of Classification Search
CPC ............ B65B 3/003; B65B 3/12; B65B 3/14; B65B 3/32; B65B 43/59
USPC ............. 141/1, 131, 165, 172, 177, 178, 179, 141/180, 242, 277
See application file for complete search history.

(56) References Cited

U.S. PATENT DOCUMENTS 2,612,016 A * 9/1952 Anderson ..................... 53/518
3,172,435 A * 3/1965 Anderson et al. ............. 141/131
(Continued)

FOREIGN PATENT DOCUMENTS

| EP | 545483 A1 | 6/1993 | |
| EP | 1193178 A1 * | 4/2002 | ............. B65B 43/58 |

OTHER PUBLICATIONS

Mar. 6, 2012, International Search Report from European Patent Office, in PCT/EP2011/069216, which is the international application for this U.S. application.
(Continued)

*Primary Examiner* — Jason K Niesz
*Assistant Examiner* — Andrew Schmid

(57) ABSTRACT

A filling device includes a first component and a second component. The first component includes a dosing cylinder having a high-viscosity material arranged therein. The second component includes a workpiece carrier and a receiving carrier. The receiving carrier is moveably connected to the workpiece carrier. The movement v of the receiving carrier during the filling process is determined by both the dynamic pressure exerted by the material and by a counterforce G generated by a unit having a pressurized fluid.

17 Claims, 2 Drawing Sheets

(56) References Cited

U.S. PATENT DOCUMENTS

| | | | | |
|---|---|---|---|---|
| 3,364,651 | A | * | 1/1968 | Stohlquist ..................... 53/284.5 |
| 4,388,795 | A | * | 6/1983 | Stohlquist et al. .............. 53/435 |
| 4,518,021 | A | * | 5/1985 | Copas et al. .................. 141/172 |
| 5,095,955 | A | * | 3/1992 | Barnewitz et al. ................ 141/1 |
| 5,127,449 | A | * | 7/1992 | Mueller et al. .................... 141/1 |
| 5,370,163 | A | * | 12/1994 | Owen ........................... 141/177 |
| 6,035,607 | A | * | 3/2000 | Miller .......................... 53/266.1 |
| 2003/0113218 | A1 | * | 6/2003 | Spreizer ..................... 417/413.1 |
| 2003/0183342 | A1 | * | 10/2003 | Spreizer ........................ 156/382 |
| 2009/0014088 | A1 | * | 1/2009 | Shun .............................. 141/180 |
| 2012/0028217 | A1 | * | 2/2012 | Spreizer .......................... 433/90 |
| 2014/0238528 | A1 | * | 8/2014 | Spreizer ............................. 141/1 |
| 2014/0248578 | A1 | * | 9/2014 | Fritze et al. ...................... 433/89 |

OTHER PUBLICATIONS

May 7, 2013 International Preliminary Report on Patentability from The International Bureau of WIPO, in PCT/EP2011/069216, which is the international application to this U.S. application (with a WIPO English translation of same).

* cited by examiner

DEVICE AND METHOD FOR THE MULTIPLE FILLING OF HIGH-VISCOSITY MATERIALS

CROSS-REFERENCE TO RELATED APPLICATION

This application is a national phase application of PCT/EP2011/069216, filed Nov. 2, 2011, which claims priority to German Patent Application No. 102010060308.2, filed Nov. 2, 2010, each of which is hereby incorporated by reference.

BACKGROUND AND SUMMARY

1. Technical Field

The invention relates to a device and a method for filling, in particular, a high-viscosity material into filling containers. The device comprises a first component comprising a material container having at least one dispensing nozzle, and a second component comprising at least one carrier for receiving the filling container.

2. Prior Art

Filling is a special form of batch dosing of a recipe comprising just a single component. Filling processes are always carried out in batches, i.e. in cycles or with multiple cycle speeds. In filling technology, the actual dosing process plays a secondary role.

What distinguishes filling from dosing in the area of product generation is that certain tolerances must be observed as regards quantitative delineation of the fill weight. In addition, statutory provisions apply, especially Weights and Measures legislation and the associated calibration regulations, which stipulate compliance with tolerances. It either is not possible or requires a great deal of effort to comply with these tolerances, especially as regards filling of high-viscosity materials, such as fillers used in dental medicine.

Object of the Invention

It is therefore an object of the invention to provide a device and a method which allow even high-viscosity materials to be filled highly accurately with respect to pre-set amounts (fill quantities).

The above object is achieved by a device as per claim 1 and a method as per claim 7. Advantageous embodiments and further developments result from the characteristics of the dependent claims.

Technical Solution

An inventive device for filling in particular a high-viscosity material into filling containers comprises: a first component comprising a material container having at least one dispensing nozzle; a second component comprising at least one carrier for receiving the filling container, said carrier being movably arranged relative to the first component by dynamic pressure generated by the material during filling; and means for exerting a defined counterforce to the dynamic pressure caused by the movement of the carrier.

The dosing device comprises essentially a first component and a second component, which comprises a carrier, which is arranged so as to move relative to the first component.

The first component comprises a dosing cylinder (material container) having side-walls and a piston head. The dosing cylinder is filled with the material to be used for filling (e.g., a composite for use in dental medicine, dental materials). In the cylinder base are arranged flow nozzles (dispensing or filling nozzles) through which the material to be filled is dispensed from the cylinder. A piston or press ram presses the material contained in the dosing cylinder through application of force to the discharge or filling nozzles out of the flow nozzles.

The second component has a pallet and/or a workpiece carrier. Arranged at the workpiece carrier is a carrier (tray, table) which is movable relative to the workpiece carrier and the purpose of which is to receive in particular several filling containers (e.g. capsules). The receptacles for the capsules are arranged side by side in one row or possibly in several adjacent rows on the carrier. The carrier can be movably connected to the pallet or workpiece carrier, for example via preferably two or more linear guides.

The dynamic pressure, which is generated in the filling containers as the material is dispensed from the flow nozzles and which is transmitted to the carrier, gives rise to a force that moves the carrier away from the nozzles and towards the pallet or workpiece carrier. The second component has a means of exerting a counterforce against this force, but the counterforce is smaller than the force exerted by the dynamic pressure, so that during the filling process the carrier with the filling containers is moved away from the nozzles, guided by the linear guide(s).

The pallet or the workpiece carrier can, for example, be connected to a movable NC axis via an NC lifting platform. As a result of the movement of the NC axis, a relative movement of the pallet or the workpiece carrier with respect to the first component can be generated. In this way, a movement superimposing the movement of the carrier with respect to the pallet or the workpiece carrier can be generated that also is transmitted to the carrier. In this way, higher fill levels can also be realized, i.e. capsules can be filled to a higher level if the maximum distance over which the carrier can be moved relative to the pallet or workpiece carrier is shorter than the fill level or the height of the capsules. For longer fill strokes, therefore, the NC axis can assume part of the path. The process itself does not become much more complex.

For example, depending on the design, the maximum pneumatically closed-loop-controlled path can be s, which is sufficient for filling smaller capsules. For filling larger capsules or syringes, a longer fill path is required. This path can be composed as the sum of a path x of the NC axis and the path s of the proportional pneumatic unit. If, for example, the proportional pneumatic unit reaches a limit value, the NC axis moves back by the amount $\Delta x$. The counterforce of the proportional pneumatic unit can be freely adjusted as a function of the path.

The fill level corresponds to the total movement path of the carrier or the filling containers and/or the second component. During the filling process, the carrier moves away from the first component under the dynamic pressure. It is "slowed down" by the counterforce. The speed at which the carrier moves is determined by the dynamic pressure (which depends on the flow behaviour of the material) and the counterforce.

Preferably, the device comprises two or more dispensing nozzles. For example, in dental medicine, large amounts of high-viscosity materials are filled into capsules. The average fill weight is usually between 200 mg and 350 mg. For economic filling of large numbers, multiple filling is beneficial. This is achieved by multiple nozzles dispensing into several filling containers in parallel. This is therefore an instance of multiple filling, which repeats itself in a series of successive cycles, as soon as one batch of filling containers has been filled. After the filling process, the carrier can be loaded with new (empty) filling containers or replaced by a carrier with unfilled filling containers. For the new filling process (cycle), the carrier is moved back into a starting position close to the dispensing nozzle(s). The number of capsules filled simultaneously is irrelevant to dosing or filling.

In particular, the means for exerting a counterforce comprise at least one controller for controlling the counterforce as a function of at least one parameter. The parameter is determined or captured or measured during the filling process.

Preferably, the means comprise a device for measuring the path travelled by the carrier from the start of the fill cycle, i.e. from the starting position. The maximum path length (fill path) of the filling container(s) or the carrier relative to the first component is pre-set. Thus, the fill volume (path multiplied by cross-sectional area of the filling container) is pre-set and is fixed for all fill cycles.

The counterforce can be exerted, e.g., by a spring, which counteracts the direction of movement of the second component. However, the drawback of this is that the counterforce cannot be varied during the filling process. Therefore, the means can preferably be configured to generate a counterforce that can be varied over the fill path. Thus, a proportional pneumatic unit for adjusting the counterforce can be provided. Thus, the counterforce can be varied during the filling process, e.g., as a function of the path. The variable counterforce, however, can be generated by all kinds of other suitable means. The counterforce can be open-loop/closed-loop controlled such that the counterforce is always generated in accordance with a path-dependent function.

The device can have a closed-loop control that regulates the dispensing pressure in the material container as a function of the fill time of the filling containers. This means that, between two fill cycles, if the fill time does not match a set value or is not within a set range, the dispensing pressure in the material container is changed so as to return the fill time to the set value or into the set range. However, the closed-loop control may also be effected by closed-loop control of other parameters of the system which influence the flow characteristics of the material.

Thus, the temperature of the material in the material container and/or in the nozzles can be changed.

In a further embodiment, the counterforce or the characteristic of the counterforce during filling can be subjected to closed-loop control.

An inventive method for filling, in particular, a high-viscosity material, into filling containers comprises the steps of:

a) exerting a dispensing pressure for dispensing the material from a material container into filling containers;

b) moving of the filling containers under the dynamic pressure generated by the material flowing into the filling containers.

The filling containers, or the carrier in which the filling containers are arranged adjacent to each other, moves away from the nozzles under the influence of the dynamic pressure.

In step b), in particular a defined counterforce is exerted against the movement of the filling containers, said movement arising from the dynamic pressure during filling of the filling containers.

By means of the invention, air-free filling is carried out against a controlled and closed-loop controlled dynamic pressure. The dynamic pressure can vary during the filling process. The restraining forces and paths are generated, e.g., by means of the electronically open-loop/closed-loop-controlled proportional pneumatic unit ("air springs") with open-loop or closed-loop force/path control.

One or several filling containers can be provided. The material can preferably be dispensed through several dispensing nozzles in parallel. Multiple filling occurs at a high throughput rate in a plurality of successive fill cycles, between each of which full filling containers are replaced by empty filling containers.

The counterforce in step b) can be open-loop or closed-loop controlled as a function of a measurement parameter.

The counterforce is open-loop or closed-loop controlled in step b), in particular as a function of the path travelled by the filling containers during the filling process. As a result of the path-dependent open-loop/closed-loop control, filling adapts to the flow behaviour of the material.

In particular, the maximum path travelled by the filling containers during the filling process is pre-set. The pre-set path corresponds to the required weight. Thus, the fill volume is determined in such a way that the filling containers are filled with high accuracy, including in a multiple filling arrangement (i.e. parallel filling). This makes it possible to meet strict requirements with regard to fill accuracy. In the prior art, methods without volumetric determination have been used. As a result, the machines may be of a very simple and inexpensive design. However, the fill quality is dependent on the skill and routine of the operating personnel. Even slight variations in flow rates lead to a rapid decline in the fill quality. The consequences are underdosing accompanied by air bubbles or overdosing and contamination of the capsules. In addition to substantial material losses and delays in production, the errors are visible to each user and troublesome in application. With the present invention, however, filling can be automated. The invention is actually a volumetric dosing method, i.e. a method in which the volumetric determination takes place through path measurement.

Preferably, the speed of the filling containers during the filling process is determined by the dynamic pressure and the counterforce exerted. In contrast to conventional methods, the speed of the filling containers during the filling process therefore adapts itself to the flow behaviour of the material.

In particular, the fill time, too, is determined by the dynamic pressure and the counterforce exerted during a filling process.

At the start of the filling process, a brief increase in counterforce occurs in order to introduce the material to be filled into the capsule opening, which is located at the lower end of the capsule (i.e. in the area that is filled first). This is thus "sealed" for the remainder of the filling process. Subsequently, the fill phase takes place under a lower counterforce.

The end of the filling process (end of the cycle) must be followed by viscoplastic tearing because stringing causes contamination. Therefore, it is expedient within the scope of the invention to temporarily increase the counterforce prior to tearing. The controller can be set such that the force increase occurs at a certain point on the fill path. The composite is then pressed firmly against the capsule wall as far as the level of the dispensing nozzle. The material has high adhesion in the nozzle and in the capsule. Through rapid force dissipation and movement of the carrier away, the material does not have enough time to become tangled and tears off. Inside the capsule and inside the nozzle, horizontal viscoplastic fracture surfaces form.

With this structure, various fill sequences can be generated.

In a particularly preferred embodiment of the invention, the dispensing pressure is closed-loop controlled as a function of the fill time of the filling containers between different fill cycles. This means that where there is any drift in the dispensing behaviour of the material from the nozzles, and thus a change in dispensing characteristics, an adjustment can be made. The drift or change manifests itself as a change in the dispensing time that is measured for filling the filling containers. Through readjustment of parameters, individually or in combination, e.g. of the dispensing pressure acting on the material in the material container, the filling process can be automatically closed-loop controlled to attain satisfactory accuracy of the fill quantity.

The problems of altered (normally accelerated) material flow behaviour that occur with conventional methods over time and after several cycles are eliminated in the present invention, since the fill paths are measured. If, after a certain number of fill cycles, a critical (usually minimal) fill time is reached, other parameters are changed in such a way that the critical dosing time is not undershot or overshot, i.e. a minimum dosing time is, e.g., not undershot. This closed-loop control can be carried out by appropriate machine software independently of an operator. The closed-loop control parameters and relationships are stored in an array in the program.

The open-loop and/or closed-loop controls are implemented by corresponding software. This can also be self-learning or self-optimising.

The system as a whole lends itself to conventional automation systems, such as rotary indexing machines, flexible assembly systems, or combinations thereof. Preferably, flexible assembly systems with pallet systems are used. Resetting of the machine can be done via pallet changes. The pallets can be calibrated outside the automation system. The geometric and physical data are transmitted to the transponders on the pallets. Thus, each pallet in the process can be tracked. These data are read out in the dosing station. The corresponding filling parameters are assigned to the pallet from a matrix. Each product has its specific dosing recipes; correction data can be assigned to each pallet.

After the dosing process, a control measurement is made of the fill level in each capsule. These data are assigned to the corresponding pallet. Where individual capsules are not filled correctly, they are segregated out at the end of the process as rejects. If errors occur on a regular basis and are assigned to this one pallet, it is taken out of production and replaced by a new one. If mistakes occur generally, production is stopped because obviously in this case the set of parameters is not suitable for the dosing/batch. A review and re-evaluation take place before damage occurs.

All the above characteristics and effects described above can be combined regardless of whether they have been explained in connection with the device or with the method.

BRIEF DESCRIPTION OF THE FIGURES

Further characteristics and advantages of the invention will become apparent from the following description of preferred embodiments using the drawings. The drawings show in.

DETAILED DESCRIPTION OF THE FIGURES

Figure 1:
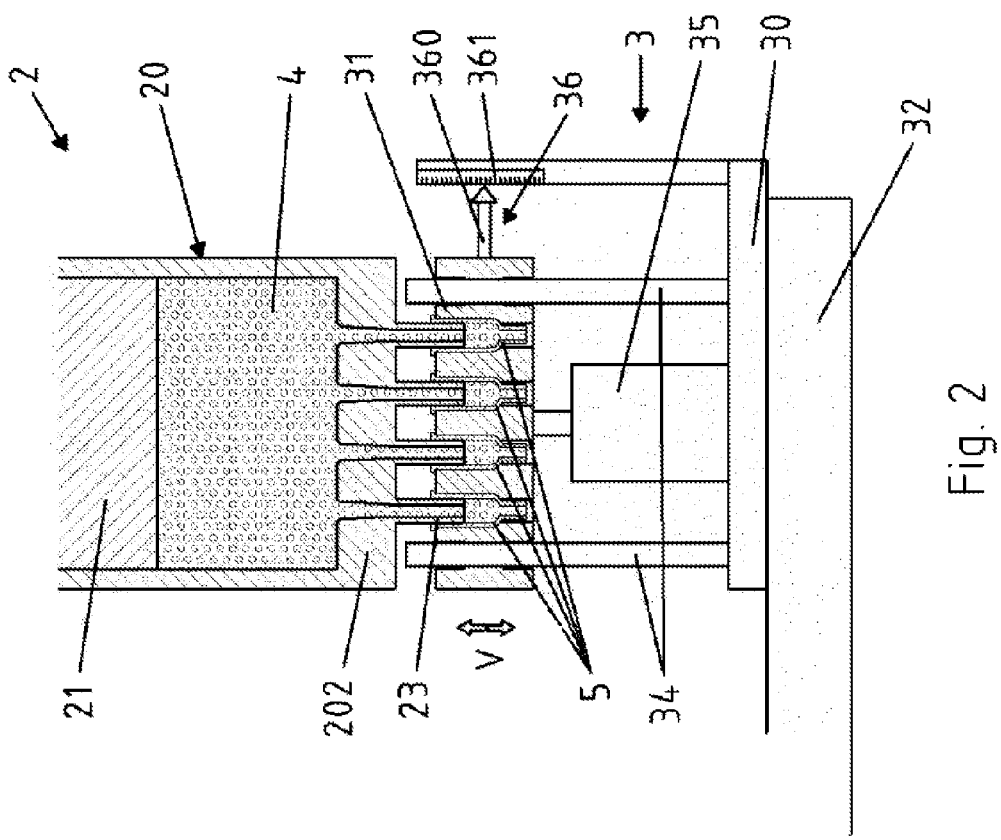
FIG. 1. a cross-sectional view of the inventive device.

FIG. 1 shows an inventive filling device 1. The filling device 1 comprises a first component 2 and a second component 3.

The first component 2 comprises a dosing cylinder 20 having a side-wall 201 and a base section 202. Moreover, the first component 2 comprises a piston 21 which is subjected via a press ram 22 to a force F, indicated by an arrow, to generate a dispensing or dosing pressure in the material (composite) 4 arranged in the container.

The second component 3 has a pallet or a workpiece carrier 30 and a receiving carrier 31. The receiving carrier 31 is movably connected to the workpiece carrier 30, as indicated by the double arrow v.

The workpiece carrier 30 is connected to an NC axis 33 via an NC lifting table 32. The NC axis 33, as indicated by the double arrow V, is arranged so as to be vertically movable with respect to the first component 2. Movement of the NC axis 33 causes the carrier 30 to move relative to the first component 2. In this way, the movements of the NC axis and the receiving carrier 31 can be superimposed on the workpiece carrier 30. The movement of the NC axis 33 is also superimposed on the receiving carrier 31. In this way, higher fill levels can be realized, i.e. capsules with a higher fill level can be filled. If the maximum movement path v of the receiving carrier 31 relative to the workpiece holder 30 is insufficient, it can be extended by movement of the NC axis.

Figure 2:
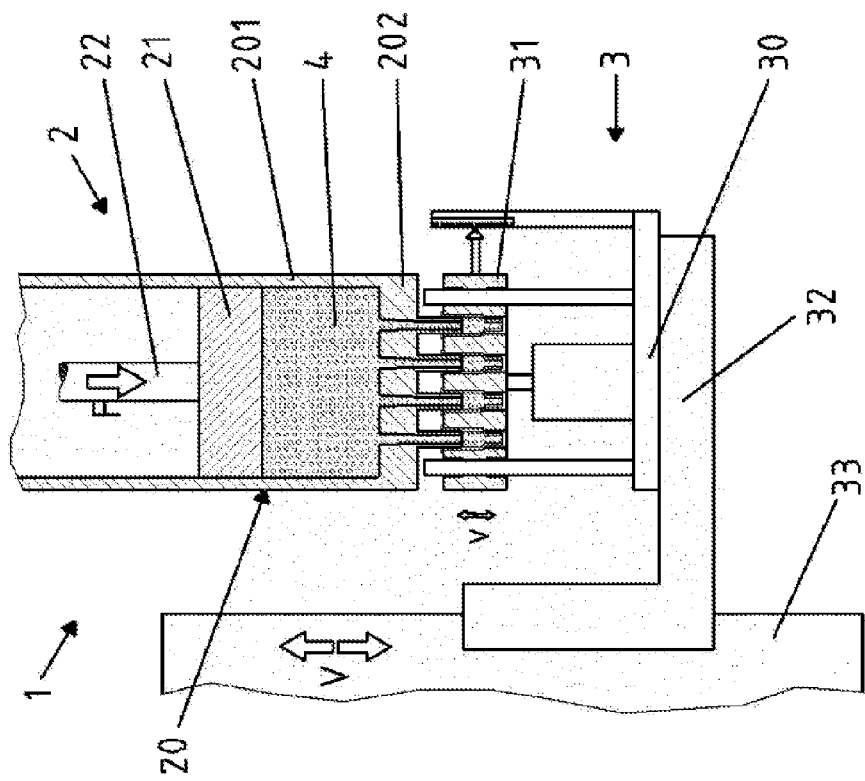
FIG. 2 a cross-sectional view of a first cut-out of the inventive apparatus.

A cut-out from FIG. 1 is shown in FIG. 2, in which the NC axis and the area around the press ram have been omitted. The same reference numerals are therefore used for the same components.

Flow nozzles 23 are formed in the base section 202 of the first component 2. These can serve to fill composite 4 into capsules 5, with the capsules 5 being arranged in corresponding adjacent receptacles in the receiving carrier 31.

The second component 3 further has linear guides 34 which extend from the workpiece carrier 30 in the direction of the first component 2. The receiving carrier 31 is connected by the linear guides 34 to the workpiece carrier 30 so as to be vertically movable (movement v). The movement v of the receiving carrier 31 relative to the flow nozzles 23 is determined on one hand by the dynamic pressure which the dispensing composite 4 exerts on the receiving carrier 31 and on the other by a counterforce G against the dynamic pressure. The counterforce G is generated by a proportional pneumatic unit 35 ("air spring") of the second component 3. The proportional pneumatic unit 35 is connected to the workpiece carrier 30 and is arranged between the workpiece carrier 30 and the receiving carrier 31.

Furthermore, the second component 3 has a measuring device 36 which is symbolically represented by a sensor 360 and a measurement scale 361. The measuring device 36 measures the path which the receiving carrier 31 has travelled, starting from a starting position which is assumed at the start of filling. According to the invention, the proportional pneumatic unit 35 is open-loop controlled in such a way that, depending on the path determined by the measuring device 36, a defined counterforce G is exerted against the movement of the receiving carrier 31 which has been generated by the dynamic pressure. The maximum path that the receiving carrier 31 travels from its starting position to the end position in which the capsules 5 are filled is pre-set. Thus, the fill volume, too, is fixed. The (instantaneous) speed v of the receiving carrier 31 is determined by the dynamic pressure and the counterforce 35 exerted by the proportional pneumatic unit. The dynamic pressure in turn depends on the flow behaviour of the composite 4.

Figure 3:
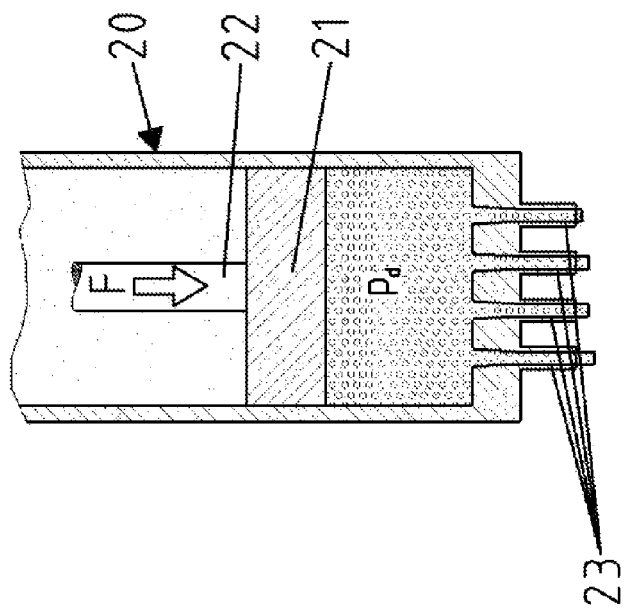
FIG. 3 a cross-sectional view of a second cut-out of the inventive device.

FIG. 3 shows further details of the inventive device. In the container area above the flow nozzles 23, a dosing pressure $p_d$ is generated by the force F. In the two filling nozzles 230 and 231 shown by way of example, there are different pressures $p_1$ and $p_2$. Due to these pressures, a dynamic pressure is generated in the capsules 5, which pushes down the receiving carrier 31, symbolized by the arrow v. The counterforce G generated by the proportional pneumatic unit 35 with force-path control is dependent on the fill distance or the path travelled by the receiving carrier 31 from the starting position. The counterforce can be set so as to vary over the fill path. During filling, it is always less than the force exerted by the dynamic pressure. The latter is calculated for the two nozzles shown, as follows: $F_{dynamic}=p_1*A+p_2*A$. Thus, the proportional pneumatic unit 35 is designed such that, during the filling process, it permits movement of the receiving carrier 31 in a downward direction only, but can exert a different counterforce G as a function of the path travelled.

Figure 4:
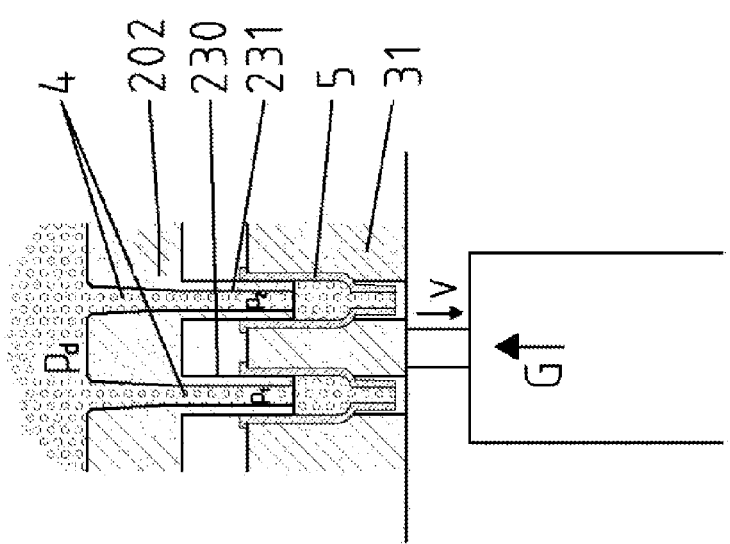
FIG. 4 a cross-sectional view of a device for explaining the dispensing behaviour.

As shown in FIG. 4, the material 4 to be filled is pressed out of the container 20 through several nozzles 23 at a constant pressure $p_d$ by application of a force F exerted on the piston 21. On account of local differences in flow characteristics, the material 4 is dispensed from the nozzles 23 at different speeds. In this way, a tolerance range arises with respect to the fill accuracy for a set value.

In the prior art, during filling, a time in which the material flows into the capsules was pre-set. During this time, the nozzles are continuously retracted from the capsules. In this connection, the volume provided and the flow rate of the material need to be constantly brought into equilibrium. The dynamic pressure should be so large that air pockets do not occur and so small that there is no overdosing. Since the flow behaviour of many materials to be filled into containers changes significantly with time, it is difficult to determine calibration cycles properly, to observe minimum fill weights, to start up processes, engage in troubleshooting, etc. Any deviations are corrected by trained and experienced personnel.

The present invention, by contrast, utilises volumetric determination (corresponding to the path measurement multiplied by the fill cross-section). The building-up of a defined counterforce automatically compensates for negative effects of variable flow rates. If the fill time of successive fill cycles changes beyond a tolerance, the installation parameters are changed in order to readjust the fill time in the opposite direction. The method is thus fully automatable.

The present disclosure may include one or more of the following concepts:

A Device for filling in particular a high-viscosity material into filling containers, comprising:
  a first component comprising a material container with at least one dispensing nozzle;
  a second component comprising at least one carrier for receiving the filling containers, wherein the carrier is movably arranged relative to the first component through the dynamic pressure of the material generated during dispensing;
  means for exerting a defined counterforce to the movement of the carrier caused by the dynamic pressure.

B. Device in accordance with paragraph A, characterized by the fact that the device comprises two or more dispensing nozzles.

C. Device in accordance with paragraph A or B, characterized by the fact that the means for exerting a counterforce comprise at least one controller for open-loop control of the counterforce as a function of at least one parameter.

D. Device in accordance with any of the previous paragraphs, characterized by the fact that the means comprise a device for measuring the path travelled by the carrier from the start of the fill cycle.

E. Device in accordance with any of the previous paragraphs, characterized by the fact that the means have a proportional pneumatic unit for setting the counterforce.

F. Device in accordance with any of the previous paragraphs characterized by the fact that the device has a closed-loop control that regulates the dispensing pressure in the material container as a function of the fill time of the filling containers.

G. Method for filling particularly a high-viscosity material into filling containers, comprising the steps:
  a) exerting a dispensing pressure for purpose of dispensing the material from a material container into filling containers; and
  b) moving of the filling containers under the dynamic pressure generated by the material flowing into the filling containers.

H. Method in accordance with paragraph G, characterized by the fact that in step b), a defined counterforce is exerted against the movement of the filling containers, said movement being caused by the dynamic pressure during filling of the filling containers.

I. Method in accordance with paragraph G or H, characterized by the fact that the material is dispensed through several dispensing nozzles in parallel.

J. Method in accordance with paragraph G or H, characterized by the fact that the counterforce in step b) is open-loop or closed-loop controlled as a function of a measurement parameter.

K. Method in accordance with any of paragraphs H to J, characterized by the fact that the counterforce in step b) is open-loop or closed-loop controlled as a function of the path travelled by the filling containers during the filling process.

L. Method in accordance with any of paragraphs G to K, characterized by the fact that the (maximum) path travelled by the filling containers during the filling process is pre-set.

M. Method in accordance with any of paragraphs G to L, characterized by the fact that the speed of the filling containers during the filling process is determined by the dynamic pressure and the exerted counterforce.

N. Method in accordance with any of paragraphs G to M, characterized by the fact that the dispensing pressure is closed-loop controlled as a function of the dispensing time during filling of the filling containers between two different fill cycles.

Although the present invention has been described in detail using the attached embodiments, it is obvious to a person skilled in the art that the invention is not restricted to these embodiments, but rather comprises modifications or changes in the context of the enclosed claims, wherein the changes can arise through different combinations of individually presented characteristics and also through the omission of individual characteristics. In particular, the invention comprises any combination of the characteristics shown.

What is claimed is:

1. A device for filling in particular a high-viscosity material into filling containers, comprising:
  a first component comprising a material container with at least one dispensing nozzle;
  a second component comprising at least one carrier for receiving the filling containers, wherein the carrier is movably arranged relative to the first component through the dynamic pressure of the material generated during dispensing;
  a unit having pressurized fluid for exerting a defined counterforce to the movement of the carrier caused by the dynamic pressure, wherein pressurized fluid from the unit for exerting the counterforce only results in the same movable arrangement of the carrier relative to the first component as the movable arrangement of the carrier relative to the first component through the dynamic pressure of the material generated during dispensing.

2. The device in accordance with claim 1, wherein the device comprises two or more dispensing nozzles.

3. The device in accordance with claim 1, wherein the unit for exerting the defined counterforce comprise at least one controller for open-loop control of the counterforce as a function of at least one parameter.

4. The device in accordance with claim 3, wherein the unit comprises a measuring device for measuring the path travelled by the carrier from the start of the fill cycle.

5. The device in accordance with claim 4, wherein the unit is a proportional pneumatic unit for setting the counterforce.

6. The device in accordance with claim 1, wherein the device has a closed-loop control that regulates the dispensing pressure in the material container as a function of the fill time of the filling containers.

7. A method for filling particularly a high-viscosity material into filling containers, comprising:
   a) exerting a dispensing pressure for purpose of dispensing the material from a material container into filling containers; and
   b) moving of the filling containers under the dynamic pressure generated by the material flowing into the filling containers, wherein a defined counterforce is exerted against the movement of the filling containers, said movement being caused by the dynamic pressure during filling of the filling containers, wherein exertion of the counterforce only results in movement of the filling containers being the same movement of the filling containers under the dynamic pressure generated by the material flowing into the filling containers during dispensing of the material.

8. The method in accordance with claim 7, wherein the material is dispensed through several dispensing nozzles in parallel.

9. The method in accordance with claim 7, wherein the counterforce in step b) is open-loop or closed-loop controlled as a function of a measurement parameter.

10. The method in accordance with claim 9, wherein the counterforce in step b) is open-loop or closed-loop controlled as a function of the path travelled by the filling containers during the filling process.

11. The method in accordance with claim 10, wherein a maximum path travelled by the filling containers during the filling process is pre-set.

12. The method in accordance with claim 11, wherein the speed of the filling containers during the filling process is determined by the dynamic pressure and the exerted counterforce.

13. The method in accordance with claim 12, wherein the dispensing pressure is closed-loop controlled as a function of the dispensing time during filling of the filling containers between two different fill cycles.

14. A device for filling in particular a high-viscosity material into filling containers, comprising:
   a first component having a material container with at least one dispensing nozzle;
   a second component having at least one carrier for receiving the filling containers, wherein the carrier is movably arranged relative to the first component through the dynamic pressure of the material generated during dispensing; further wherein a defined counterforce is exerted by a unit having pressurized fluid to the movement of the carrier caused by the dynamic pressure, wherein exertion of the counterforce by the pressurized fluid of the unit only results in the same movable arrangement of the carrier relative to the first component as the movable arrangement of the carrier relative to the first component through the dynamic pressure of the material generated during dispensing,
   at least one controller for open-loop control of the counterforce as a function of at least one parameter, and
   a measuring device for measuring the path travelled by the carrier from the start of the fill cycle.

15. The device of claim 14, wherein the unit is a proportional pneumatic unit for setting the counterforce.

16. The device of claim 15, wherein the device has a closed-loop control that regulates the dispensing pressure in the material container as a function of the fill time of the filling containers.

17. The device of claim 16, wherein the device comprises two or more dispensing nozzles.

* * * * *